United States Patent [19]

Pfister et al.

[11] Patent Number: 4,602,931
[45] Date of Patent: Jul. 29, 1986

[54] HERBICIDAL AND FUNGICIDAL CHLORINATED PHOSPHORYLMETHYLCARBONYL-PYRAZOLES

[75] Inventors: Theodor Pfister, Monheim; Ludwig Eue, Leverkusen; Hans-Joachim Santel, Cologne; Robert R. Schmidt, Bergisch-Gladbach; Gerd Hänssler, Leverkusen, all of Fed. Rep. of Germany

[73] Assignee: Bayer Aktiengesellschaft, Leverkusen, Fed. Rep. of Germany

[21] Appl. No.: 708,324

[22] Filed: Mar. 5, 1985

[30] Foreign Application Priority Data

Mar. 13, 1984 [DE] Fed. Rep. of Germany ....... 3409081

[51] Int. Cl.$^4$ .......................... C07F 9/65; A01N 57/08
[52] U.S. Cl. ......................................... 71/86; 514/94; 548/112
[58] Field of Search ............... 548/112; 514/94; 71/86

[56] References Cited

U.S. PATENT DOCUMENTS 4,371,526  2/1983  Rovnyak ............................ 548/112
4,439,428  3/1984  Cox .................................... 548/112

FOREIGN PATENT DOCUMENTS 0011363  5/1980  European Pat. Off. ............ 548/112
0126249  11/1984  European Pat. Off. ............ 548/112
310406  12/1955  Switzerland ................. 260/502.4 R Primary Examiner—Richard A. Schwartz
Assistant Examiner—Kurt G. Briscoe
Attorney, Agent, or Firm—Sprung Horn Kramer & Woods

[57] ABSTRACT

Chlorinated phosphorylmethylcarbonylpyrazoles of the formula

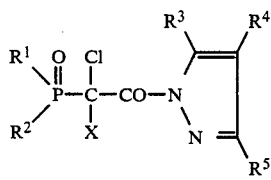

in which
$R^1$ is an optionally substituted alkyl, aryl, aralkyl, alkoxy or aralkoxy radical,
$R^2$ is an optionally substituted alkoxy or aralkoxy radical, or
$R^1$ and $R^2$ together are an alkanedioxy radical,
X is hydrogen or chlorine,
$R^3$ and $R^5$ each independently is hydrogen or alkyl, and
$R^4$ is hydrogen, halogen or alkyl,
which possess herbicidal and fungicidal activity.

8 Claims, No Drawings

HERBICIDAL AND FUNGICIDAL CHLORINATED PHOSPHORYLMETHYLCARBONYLPYRAZOLES

The invention relates to new phosphorylmethylcarbonylpyrazole derivatives, a process for their preparation, and their use as plant protection agents, in particular as herbicides and fungicides.

It is known that certain chlorinated phosphorylacetic acid esters can be used as herbicides (see, for example, European Patent No. 1,018). Thus, for example, (1-methyl)-ethyl 2,2-dichloro-2-(diethoxyphosphoryl)-acetate can be used for combating weeds. It is also known that certain bis-dithiocarbamates, such as, for example, zinc ethylene-bis-dithiocarbamate, possess fungicidal activity (see U.S. Pat. Nos. 2,457,674 and 3,050,439). However, the action of these compounds is not always satisfactory, particularly in the case of low application rates and concentrations.

New chlorinated phosphorylmethylcarbonylpyrazole derivatives of the formula (I)

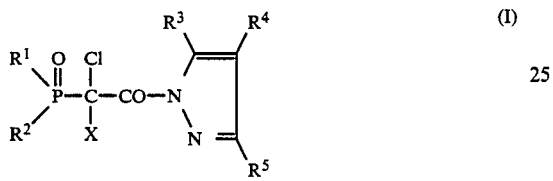

in which
R$^1$ represents optionally substituted radicals from the series comprising alkyl, aryl, aralkyl, alkoxy and aralkoxy,
R$^2$ represents optionally substituted radicals from the series comprising alkoxy and aralkoxy, or
R$^1$ and R$^2$ together represent an alkanedioxy radical,
X represents hydrogen or chlorine,
R$^3$ and R$^5$ are identical or different and represent hydrogen or alkyl and
R$^4$ represents hydrogen, halogen or alkyl,
have now been found.

The new compounds of the formula (I) are obtained by a method in which phosphorylmethylcarbonylpyrazole derivatives of the formula (II)

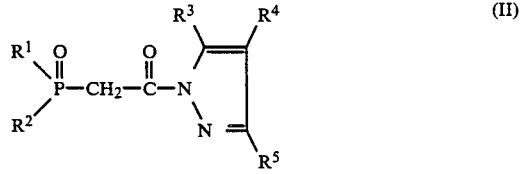

in which
R$^1$, R$^2$, R$^3$, R$^4$ and R$^5$ have the meanings given above, are reacted with a chlorinating agent, if appropriate in the presence of an acid acceptor and, if appropriate, in the presence of a diluent.

The new chlorinated phosphorylmethylcarbonylpyrazole derivatives of the formula (I) are distinguished by high herbicidal and fungicidal activity.

Surprisingly, the active compounds according to the invention, of the formula (I), are superior to the previously known chlorinated phosphorylacetates (according to European Patent No. 1,018) against economically important graminaceous weeds in dicotyledon cultures, such as cotton and soy beans. Furthermore, they have a better systemic action against plant diseases than the abovementioned bisthiocarbamates (according to U.S. Pat. Nos. 2,457,674 and 3,050,439).

The invention preferably relates to the new chlorinated phosphorylmethylcarbonylpyrazole derivatives of the formula (I) in which
R$^1$ represents radicals from the series comprising alkyl having up to 6 carbon atoms, alkoxy having up to 6 carbon atoms, aralkyl or aralkoxy having 6 to 10 carbon atoms in the aryl part and up to 2 carbon atoms in the alkyl part [such as, in particular, benzyl, phenylethyl, benzyloxy and phenylethoxy] which are optionally monosubstituted or polysubstituted by halogen [such as, in particular, fluorine, chlorine and/or bromine] or by C$_1$-C$_4$-alkoxy, or represents phenyl which is optionally monosubstituted or polysubstituted by halogen [such as, in particular, fluorine, chlorine and/or bromine], nitro, C$_1$-C$_4$-alkyl, C$_1$-C$_4$-alkoxy and/or C$_1$-C$_4$-alkoxycarbonyl,
R$^2$ represents alkoxy which has up to 6 carbon atoms and is optionally monosubstituted or polysubstituted by halogen [such as, in particular, fluorine, chlorine and/or bromine] or by C$_1$-C$_4$-alkoxy, and represents aralkoxy having 6 to 10 carbon atoms in the aryl part and up to 2 carbon atoms in the alkyl part [such as, in particular, benzyloxy or phenylethoxy], or
R$^1$ and R$^2$ together represent a branched or straight-chain alkanedioxy radical having 2 to 5 carbon atoms in the alkyl part,
X represents hydrogen or chlorine,
R$^3$ and R$^5$ are identical or different and represent hydrogen or C$_1$-C$_4$-alkyl and
R$^4$ represents hydrogen, halogen, [such as, in particular, chlorine] or C$_1$-C$_4$-alkyl.

The invention relates in particular to compounds of the formula (I) in which
R$^1$ represents ethoxy, n-propoxy, i-propoxy, n-butoxy, i-butoxy, sec.-butoxy, tert.-butoxy or phenyl,
R$^2$ represents ethoxy, n-propoxy, i-propoxy, n-butoxy, i-butoxy, sec.-butoxy or tert.-butoxy,
X represents hydrogen or chlorine and
R$^3$ and R$^5$ are identical or different and represent hydrogen or methyl, and
R$^4$ represents hydrogen or chlorine.

If, for example, sodium hypochlorite is used as the chlorinating agent, and 1-di-propoxy-phosphorylmethylcarbonylpyrazole is used as a starting material, the course of the reaction in the process according to the invention can be represented by the following equation:

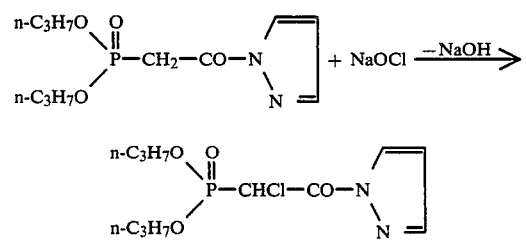

Formula (II) gives a definition of the phosphorylmethylcarbonylpyrazole derivatives to be used as starting materials. In this formula, R$^1$, R$^2$, R$^3$, R$^4$ and R$^5$ preferably or particularly preferably represent those radicals which have already been mentioned in connection with the definitions of substituents in the formula (I) as being preferred or particularly preferred.

The following may be mentioned as examples of starting materials for the compounds of the formula (II):

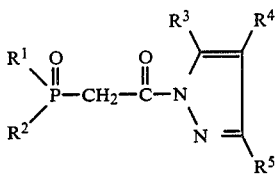

TABLE 1

| $R^1$ | $R^2$ | $R^3$ | $R^4$ | $R^5$ |
|---|---|---|---|---|
| $OC_2H_5$ | $OC_2H_5$ | $CH_3$ | H | $CH_3$ |
| $OCH(CH_3)_2$ | $OCH(CH_3)_2$ | H | H | H |
| $OCH(CH_3)_2$ | $OCH(CH_3)_2$ | $CH_3$ | H | $CH_3$ |
| $OC_2H_5$ | $OC_2H_5$ | H | H | H |
| $OC_2H_5$ | $OC_2H_5$ | H | Cl | H |
| $OC_2H_5$ | $OC_2H_5$ | $CH_3$ | Cl | $CH_3$ |
| $OC_2H_5$ | $OC_2H_5$ | $CH_3$ | $CH_3$ | $CH_3$ |
| $OC_3H_7$ | $OC_3H_7$ | H | Cl | H |
| $OC_3H_7$ | $OC_3H_7$ | $CH_3$ | Cl | H |
| $OC_3H_7$ | $OC_3H_7$ | $CH_3$ | $CH_3$ | $CH_3$ |

Some of the starting materials of the formula (II) have been hitherto unknown. These compounds are obtained if halogenomethylcarbonylpyrazole derivatives of the formula (III)

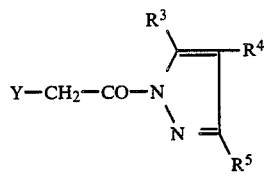

in which
$R^3$, $R^4$ and $R^5$ have the meanings given above and
Y represents halogen, in particular chlorine or bromine,
are heated with compounds of the formula (IV)

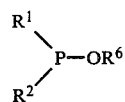

in which
$R^1$ and $R^2$ have the abovementioned meanings and
$R^6$ represents optionally substituted $C_1$-$C_4$-alkyl or benzyl,
to temperatures between 50° C. and 200° C., preferably between 100° C. and 150° C., and the reaction products of the formula Y—$R^6$ are removed, if appropriate under reduced pressure.

Some of the halogenomethylcarbonylpyrazole derivatives of the formula (III) have not yet been described in the literature. These compounds are obtained when halogenoacetyl halides of the formula (V)

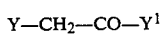

in which
Y and $Y^1$ are identical or different and represent halogen, in particular chlorine or bromine,
are reacted with pyrazoles of the formula (VI)

in which
$R^3$, $R^4$ and $R^5$ have the meanings given above,
in the presence of acid acceptors, such as, for example, triethylamine, and in the presence of diluents, such as, for example, methylene chloride, at temperatures between −50° C. and +100° C., preferably between −20° C. and +50° C.

Working up can be carried out by customary methods, for example by washing the organic solution with aqueous sodium bicarbonate solution, drying, filtering the organic phase and distilling off the solvent under reduced pressure.

The compounds of the formula (IV) are well-known compounds of organic chemistry.

The following may be mentioned as examples: triethyl, tri-n-propyl, tri-i-propyl, tri-n-butyl, tri-i-butyl and tri-sec.-butyl phosphite, and di-ethyl, di-n-propyl, di-i-propyl, di-n-butyl, di-i-butyl and di-sec.-butyl phenylphosphonite.

The starting materials of the formulae (V) and (VI) are well-known compounds of organic chemistry.

The process for the preparation of the new compounds of the formula (I) is carried out using chlorinating agents. Chlorinating agents which may be mentioned are chlorine, sulphuryl chloride and alkali metal or alkaline earth metal hypochlorites, such as, for example, sodium hypochlorite (if appropriate in the form of the so-called chloride of soda) or calcium hypochlorite. Chloride of soda is preferably used.

The process according to the invention is preferably carried out in the presence of diluents. Particularly suitable diluents are halogenated hydrocarbons, such as, for example, methylene chloride, ethylene chloride, chloroform or tetrachloromethane. When chloride of soda is employed, the diluent used is water, if appropriate supplemented by an inert organic solvent.

If required, acid acceptors are used in the process according to the invention. When aqueous hypochlorite solutions are employed, the corresponding alkali metal hydroxides or alkaline earth metal hydroxides, such as, for example, sodium hydroxide, potassium hydroxide or calcium hydroxide, are preferably used as acid-binding agents.

In the process according to the invention, the reaction temperatures can be varied within a substantial range. In general, the reaction is carried out at between −20° C. and +50° C., preferably at 0° C. to 30° C. The process is carried out in general under atmospheric pressure.

To carry out the process according to the invention, in general between 0.5 and 5, preferably between 0.9 and 3.5, mol equivalents of chlorinating agent are employed per mol of phosphorylmethylcarbonylpyrazole derivative of the formula (II), and the pH value is kept in general between 7 and 14, preferably between 9 and 14.

In general, the chlorinating agent and the diluent are initially introduced, and the compound of the formula (II) is added while stirring vigorously. When the reaction is complete, working up can be carried out by customary methods, for example by washing the organic solution with aqueous sodium bicarbonate solution, drying and filtering the organic phase, and distilling off the solvent under reduced pressure at a moderately elevated temperature. The sparingly volatile residues essentially contain the compounds of the formula (I), which are characterized by their physicochemical properties.

The active compounds according to the invention can be used as defoliants, desiccants and agents for destroying broad-leaved plants, and especially as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the general: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed for selectively combating grasses in crop plants such as, for example, cotton and soy beans.

The active compounds according to the invention furthermore exhibit a powerful microbicidal action and can be employed in practice for combating undersired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration by plants of the active compounds at the concentrations required for combating plant diseases permits treatment of above-ground parts of plants, of vegetative propagation stock and seeds of the soil.

As plant protection agents, the active compounds according to the invention can be used with particularly good success for systemically combating rice diseases, such as *Pyricularia oryzae*.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixing being possible.

Herbicides which are suitable for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethylurea for combating weeds in cereals, 4-amino-3-methyl-6-phenyl-1,2,4-triazin-5-(4H)-one for combating weeds in sugar beet, and 4-amino-6-(1,1-dimethylethyl)-3-methylthio-1,2,4-triazin-5-(4H)-one for combating weeds in soy beans. Surprisingly, some of these mixtures also exhibit a synergistic effect.

Mixtures with other known active compounds, such as fungicides, insecticides, acaricides, nematicides, bird repellents, plant nutrients and agents which improve soil structure, are also possible.

The active compounds can be used as such or in the form of their formulations or the use forms prepared therefrom by further dilution, such as ready-to-use solutions, suspensions, emulsions, powders, pastes and granules. They are used in the customary manner, for example by watering, spraying, atomizing, scattering, immersion, misting, vaporizing, injecting, forming a slurry, brushing on, dusting, dry dressing, moist dressing, wet dressing, slurry dressing or encrusting.

When used as herbicides, the active compounds according to the invention can be applied either before or after emergence of the plants. They are preferably used before emergence of the plants, that is to say by the preemergence method. They can also be incorporated into the soil before sowing.

The amount of active compound used can vary within a substantial range. It depends essentially on the nature of the desired effect. In general, the amounts used are between 0.05 and 10 kg of active compound per ha, preferably between 0.1 and 5 kg per ha.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The examples which follow serve to illustrate the invention further.

PREPARATION EXAMPLES

Example 1

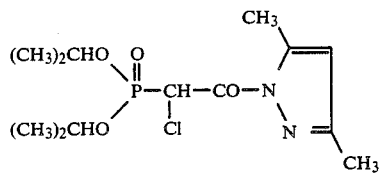

A solution of 10 g (0.033 mol) of 1-(diisopropoxyphosphorylmethylcarbonyl)-3,5-dimethyl-pyrazole in 50 ml of tetrachloromethane was added dropwise to a stirred mixture, cooled to 0° C. to 5° C., of 37.6 g of 11.5% strength sodium hypochlorite and 100 ml of tetrachloromethane, and the reaction mixture was stirred for two hours at 0° C. to 5° C. The organic phase was separated off, washed with ice-cold sodium bicarbonate solution, dried with sodium sulphate and filtered. The solvent was distilled off carefully from the filtrate under reduced pressure.

5.2 g (47% of theory) of 1-(diisopropoxyphosphorylchloromethylcarbonyl)-3,5-dimethyl-pyrazole were obtained as a yellow oil of refractive index $n_D^{20} = 1.4574$.

It is possible to prepare the compounds of the formula (I) which are listed in Table 2 below analogously to Example 1:

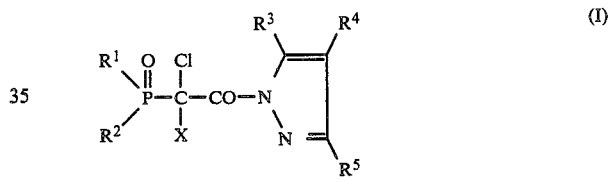

TABLE 2

| Example No. | $R^1$ | $R^2$ | X | $R^3$ | $R^4$ | $R^5$ | Refractive index $n_D^{20}$: |
|---|---|---|---|---|---|---|---|
| 2 | —OCH(CH$_3$)$_2$ | —OCH(CH$_3$)$_2$ | Cl | H | H | H | 1.5095 |
| 3 | —OCH(CH$_3$)$_2$ | —OCH(CH$_3$)$_2$ | Cl | CH$_3$ | H | CH$_3$ | 1.4786 |
| 4 | —OC$_2$H$_5$ | —OC$_2$H$_5$ | Cl | CH$_3$ | H | CH$_3$ | |
| 5 | —OCH(CH$_3$)$_2$ | —OCH(CH$_3$)$_2$ | H | CH$_3$ | Cl | CH$_3$ | |
| 6 | —OCH(CH$_3$)$_2$ | —OCH(CH$_3$)$_2$ | H | H | Cl | H | |
| 7 | —OC$_2$H$_5$ | —OC$_2$H$_5$ | Cl | H | H | H | |
| 8 | —OC$_2$H$_5$ | —OC$_2$H$_5$ | H | CH$_3$ | CH$_3$ | CH$_3$ | |
| 9 | —OCH(CH$_3$)$_2$ | —OCH(CH$_3$)$_2$ | H | CH$_3$ | CH$_3$ | CH$_3$ | |
| 10 | —OCH(CH$_3$)$_2$ | —OCH(CH$_3$)$_2$ | Cl | CH$_3$ | CH$_3$ | CH$_3$ | |
| 11 | —OC$_2$H$_5$ | —OC$_2$H$_5$ | Cl | CH$_3$ | CH$_3$ | CH$_3$ | |

PREPARATION OF THE STARTING MATERIALS OF THE FORMULA (II)

Example II-1

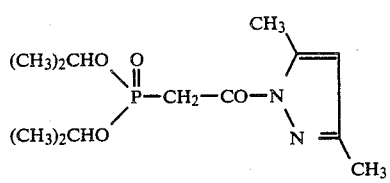

18.4 g (0.09 mol) of triisopropyl phosphite were added to 13.8 g (0.08 mol) of 1-chloromethylcarbonyl- 3,5-dimethylpyrazole at approx. 50° C., and the reaction mixture was heated to 140° C. for 4 hours, while stirring. Volatile components were then distilled off under reduced pressure.

23.7 g (98% of theory) of 1-(diisopropoxyphosphorylmethylcarbonyl)-3,5-dimethyl-pyrazole were obtained as an oil of refractive index $n_D^{20}=1.4645$.

It is possible to prepare the compounds of the formula (II) which are listed in Table 3 below by an analogous method:

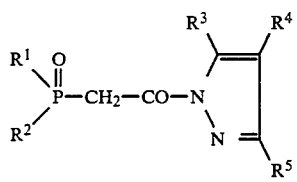

(II)

TABLE 3

| Example No. | R¹ | R² | R³ | R⁴ | R⁵ | Refractive Index $n_D^{20}$ |
|---|---|---|---|---|---|---|
| II-2 | —OCH(CH₃)₂ | —OCH(CH₃)₂ | H | H | H | 1.4700 |
| II-3 | —OC₂H₅ | —OC₂H₅ | H | H | H | |
| II-4 | —OC₂H₅ | —OC₂H₅ | CH₃ | H | CH₃ | |
| II-5 | —OC₂H₅ | —OC₂H₅ | H | Cl | H | |
| II-6 | —OC₂H₅ | —OC₂H₅ | CH₃ | Cl | CH₃ | |
| II-7 | —OC₂H₅ | —OC₂H₅ | CH₃ | CH₃ | CH₃ | |
| II-8 | —OCH(CH₃)₂ | —OCH(CH₃)₂ | H | Cl | H | |
| II-9 | —OCH(CH₃)₂ | —OCH(CH₃)₂ | CH₃ | Cl | CH₃ | |

PREPARATION OF STARTING MATERIALS OF THE FORMULA (III)

Example III-1

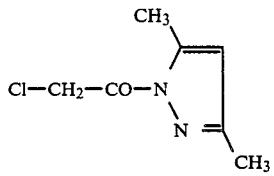

22.4 g (0.2 mol) of chloroacetyl chloride were added to a stirred mixture of 19.2 g (0.2 mol) of 3,5-dimethylpyrazole, 20.4 g (0.2 mol) of triethylamine and 50 ml of methylene chloride at 30° C. The reaction mixture was stirred for approx. 15 hours at 15° C. to 25° C., washed with sodium bicarbonate solution, dried with sodium sulphate and filtered, and volatile components were distilled off from the filtrate under reduced pressure, the product crystallising.

28.4 g (82% of theory) of 1-chloromethylcarbonyl-3,5-dimethyl-pyrazole of melting point 62° C. were obtained.

It is possible to prepare the compounds of the formula (III) which are listed in Table 4 below by an analogous method:

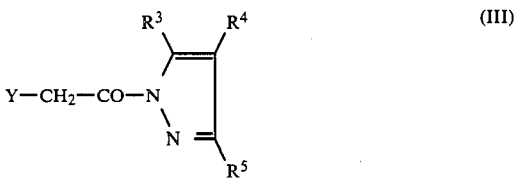

(III)

TABLE 4

| Example No. | Y | R³ | R⁴ | R⁵ | Refractive index $n_D^{20}$ |
|---|---|---|---|---|---|
| III-2 | Cl | H | H | H | 1,5289 |
| III-3 | Br | H | H | H | |
| III-4 | Br | CH₃ | H | CH₃ | |
| III-5 | Cl | CH₃ | Cl | CH₃ | |
| III-6 | Cl | CH₃ | CH₃ | CH₃ | |
| III-7 | Cl | H | Cl | H | |

Example A

Pre-emergence test/greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the following compound according to the preparation examples exhibits an excellent activity: (1).

Example B

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae.* Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compound according to the following preparation example: (3)

It is understood that the specification and examples are illustrative but not limitative of the present invention and that other embodiments within the spirit and scope of the invention will suggest themselves to those skilled in the art.

We claim:

1. A chlorinated phosphorylmethylcarbonylpyrazole of the formula 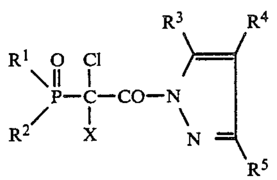 in which $R^1$ is alkyl having 1 to 6 carbon atoms, alkoxy having 1 to 6 carbon atoms, carbocyclic aralkyl or aralkoxy having 6 to 10 carbon atoms in the aryl part and up to 2 carbon atoms in the alkyl part and which is optionally substituted by halogen or by $C_1$–$C_4$-alkoxy, or is phenyl which is optionally substituted by halogen, nitro, $C_1$–$C_4$-alkyl, $C_1$–$C_4$-alkoxy and/or $C_1$–$C_4$-alkoxycarbonyl, $R^2$ is alkoxy which has 1 to 6 carbon atoms and is optionally substituted by halogen or by $C_1$–$C_4$-alkoxy, or is carbocyclic aralkoxy having 6 to 10 carbon atoms in the aryl part and up to 2 carbon atoms in the alkyl part, or $R^1$ and $R^2$ together are an alkanedioxy radical having 2 to 5 carbon atoms, $R^3$ and $R^5$ each independently is hydrogen or $C_1$–$C_4$-alkyl, X is hydrogen or chlorine, and $R^4$ is hydrogen, halogen or $C_1$–$C_4$-alkyl.

2. A compound according to claim 1, in which $R^1$ is ethoxy, n-propoxy, i-propoxy, n-butoxy, i-butoxy, sec.-butoxy, tert.-butoxy or phenyl, $R^2$ is ethoxy, n-propoxy, i-propoxy, n-butoxy, i-butoxy, sec.-butoxy or tert.-butoxy, $R^3$ and $R^5$ each independently is hydrogen or methyl, and $R^4$ is hydrogen or chlorine.

3. A compound according to claim 1, wherein such compound is 1-(diisopropoxyphosphoryl-chloromethylcarbonyl)-3,5-dimethyl-pyrazole of the formula

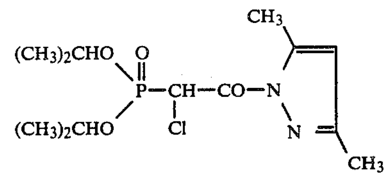

4. A compound according to claim 1, wherein such compound is 1-(diisopropoxyphosphoryl-dichloromethylcarbonyl)-pyrazole of the formula

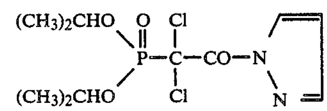

5. A compound according to claim 1, wherein such compound is 1-(diisopropoxyphosphoryl-dichloromethylcarbonyl)-3,5-dimethyl-pyrazole of the formula

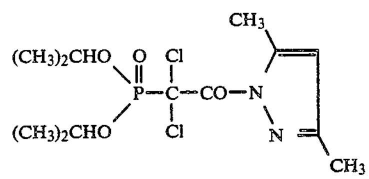

6. A herbicidal or fungicidal composition comprising a herbicidally or fungicidally effective amount of a compound according to claim 1 and an extender.

7. A method of combating unwanted vegetation or fungi, which comprises applying to such vegetation, fungi or a site from which such vegetation or fungi are to be excluded a herbicidally or fungicidally effective amount of a compound according to claim 1.

8. The method according to claim 7, wherein such compound is 1-(diisopropoxyphosphoryl-chloromethylcarbonyl)-3,5-dimethyl-pyrazole, 1-(diisopropoxyphosphoryl-dichloromethylcarbonyl)-pyrazole or 1-(diisopropoxyphosphoryl-dichloromethylcarbonyl)-3,5-dimethyl-pyrazole.

* * * * *